(12) United States Patent
Kuzyk

(10) Patent No.: US 8,328,777 B2
(45) Date of Patent: Dec. 11, 2012

(54) UMBILICAL CORD CELL HARVESTING

(76) Inventor: Roman Kuzyk, Hamilton Square, NJ (US)

(*) Notice: Subject to any disclaimer, the term of this patent is extended or adjusted under 35 U.S.C. 154(b) by 314 days.

(21) Appl. No.: 12/568,632

(22) Filed: Sep. 28, 2009

(65) Prior Publication Data

US 2010/0081966 A1   Apr. 1, 2010

Related U.S. Application Data

(60) Provisional application No. 61/100,444, filed on Sep. 26, 2008.

(51) Int. Cl.
*A61M 1/00* (2006.01)
(52) U.S. Cl. ...................................................... 604/317
(58) Field of Classification Search .................. 604/317; 600/573, 576, 578, 580
See application file for complete search history.

(56) References Cited

U.S. PATENT DOCUMENTS 5,267,967 A     12/1993  Schneider
2008/0228153 A1*  9/2008  Shacham ..................... 604/317

OTHER PUBLICATIONS

Cable Clamp (r) Reference, 2007.*
International search report dated Nov. 23, 2010 in corresponding International Application No. PCT/US10/050321.

* cited by examiner

*Primary Examiner* — Brian Szmal
(74) *Attorney, Agent, or Firm* — Donald R. Piper, Jr.; Dann, Dorfman, Herrell & Skillman, PC

(57) ABSTRACT

An apparatus and method are provided for harvesting biological material from an umbilical cord. A drain functions to drain the material from the umbilical cord. The apparatus includes a seal member for sealing an open end of an umbilical cord with the drain. A support is provided to support the seal member. An actuator is provided to adjust the engagement of the seal member with the umbilical cord. Moving the actuator relative to the support allows the seal member to twist about the umbilical cord to seal against the umbilical cord to effect drainage of material from the umbilical cord to the drain without leakage.

18 Claims, 4 Drawing Sheets

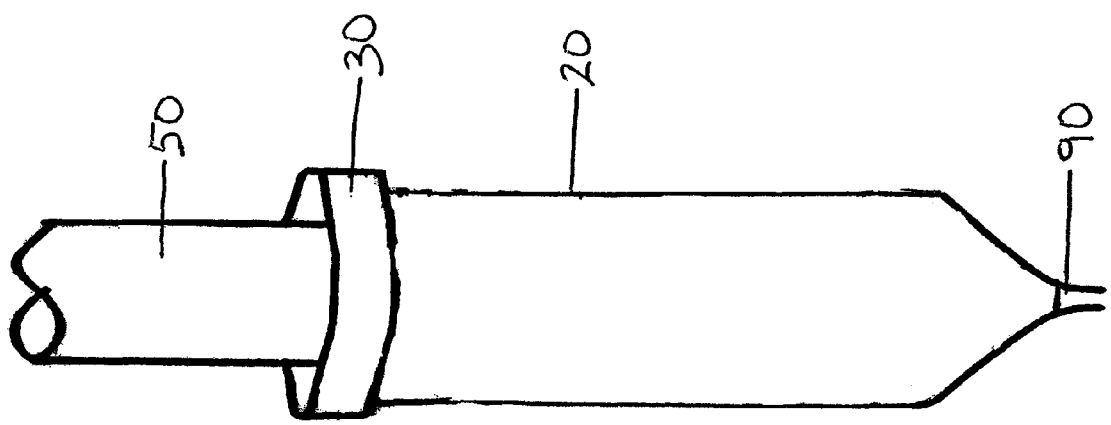

UMBILICAL CORD CELL HARVESTING

PRIORITY CLAIM

This application claims priority to U.S. Provisional Patent Application No. 61/100,444, filed Sep. 26, 2008, the entire disclosure of which is hereby incorporated by reference.

FIELD OF THE INVENTION

The present invention relates to an apparatus and method for collecting biological materials, such as fluids, blood, stem cells, and other cells, from an umbilical cord.

BACKGROUND OF THE INVENTION

Umbilical cords contain biological materials that are used in a variety of medical procedures. Specifically, umbilical cords contain fluid, blood, cells and specifically stem cells that may be used in other applications. As the number of procedures using biological materials derived from umbilical cords grows, collecting biological material from umbilical cords has become a commonplace medical practice. A newly-delivered umbilical cord may be used, or a cord may be used after a child is born but before the placenta is delivered. Typically, a medical practitioner will clamp and cut the cord at a selected position. One or more needles are inserted into the umbilical cord to extract biological material. The extracted material is then placed into a bag for storage.

Despite the growing uses for biological material from umbilical cords, current tools and methods for collecting biological material from an umbilical cord have several drawbacks. In this regard, medical practitioners use needles and syringes to harvest material from umbilical cords. The use of needles has the limitation that a conventional needle has a relatively small diameter relative to the diameter of the cord. The needle may not extend through the length of the umbilical cord or be configured or positioned to collect material from across the whole diameter of the cord.

Another drawback of the traditional methods used to collect material from umbilical cords is that the use of needles and syringes present potentially dangerous situations for medical personnel. Whenever a needle is used for a medical procedure, a risk exists that the personnel may be inadvertently stuck by the needle and contract disease or blood-borne illness. As such, using needles to collect biological material from umbilical cords may be inefficient and may also create a potential hazard for medical personnel.

Accordingly, an apparatus and method for thoroughly and safely harvesting biological material from an umbilical cord is desirable.

SUMMARY OF THE INVENTION

In accordance with the present invention, an apparatus and method are provided for collecting fluid from a fluid-filled tube such as a vein, vessel, cord member, or other tubular member, and more particularly, for harvesting biological materials including fluid, blood, stem cells, and/or cellular material from an umbilical cord and preferably across the entire diameter of the cord.

In one embodiment, a seal member may be provided to seal an open end of an umbilical cord relative to a collection drain. The seal member may be sealably engageable with an umbilical cord and sealable or sealed relative to the drain to facilitate drainage of desired material from the umbilical cord and to prevent leakage. The seal member may be in the form of a sealing sleeve which may preferably be adjustable or movable into sealing engagement with an exterior surface of an umbilical cord. Optionally, the sealing sleeve may be stretchable in an axial direction and twistable and stretchable in a rotational direction. The sleeve may be sufficiently elastic so as to return to or approximately to its original shape after stretching or deformation. The seal member functions to seal an open end of an umbilical cord with a drain to effect drainage of fluid extracted from the cord. A support may be provided for supporting the seal member in a desired position or orientation. An actuator may be provided to actuate or facilitate actuation or adjustment of the seal member into a sealing relationship with the cord so fluid may drain from the cord without leakage or optimally without exposure to atmosphere. Movement of the actuator relative to the support may function to cause sealed engagement of the seal member with the cord. The seal member may be bonded or otherwise sealed relative to the drain to prevent leakage of material from the apparatus. Sealed engagement of the seal member with the cord prevents overflow of material flowing from the umbilical cord toward the drain.

Optionally, the support may include a support tube in communication with the actuator and configured to support the seal member within the support tube. The support tube may also function to protect the seal member as well as to contain any fluid that may inadvertently leak from the seal member during use. In one embodiment, the actuator may be movable in a controlled manner relative to the support. For this purpose, support cogs may be provided at a position along the support to function, for example, as a track for the actuator. Similarly, actuator cogs may be provided along the actuator to mate with and movably engage the support cogs to enable movement and, optionally, ratchet-like movement, of the actuator cogs relative to the support cogs thereby enabling controlled movement of the actuator relative to the support. Optionally, the support cogs may be positioned along an upper surface of the support tube, for example, as a ring around an exposed top surface of the support tube. In such an arrangement, the support cogs provide an annular track and function to mate with the actuator cogs positioned, for example, as a mating ring on an undersurface of the actuator to enable the actuator to rotate, and optionally, ratchet, along the support cogs as the actuator is rotated relative to the support tube. The actuator may move in one or more directions such as a rotational direction to permit rotation of the actuator about the track as well as an axial direction to permit the actuator to be removably disengaged from the track and/or the support tube or to permit the actuator and support cogs to slide or move past each other. Optionally, the cogs may prohibit movement in an opposite rotational direction thereby providing a racket-like relative movement between actuator and the support tube.

The actuator cooperates with the seal member in order to move or twist the seal member in a desired manner. In this regard, moving the actuator relative to the support tube functions to move the seal member within the support tube so as to sealably engage relative to the umbilical cord. By moving the seal member into sealed engagement with the outer surface of the umbilical cord, the seal member may be used with cords of varying diameter. More specifically, for example, the actuator may rest on top of or be supported in position at the top of the support tube with the actuator cogs at a bottom of the actuator in engagement with the support cogs at the top of the support tube. As the actuator is twisted or turned relative to the support, a ring of actuator cogs rides on a ring of support cogs to permit rotational movement of the actuator relative to the support tube which in turn causes the seal member to adjustably engage or twist about an umbilical cord. The cogs may be configured to prevent backward rotational movement of the actuator relative to the support tube to prevent backlash by the twisting seal member.

In another embodiment, the seal member may include a moveable or twistable sealing sleeve such as an elastic tubing. The tubing may be dimensioned to enclose and engage at least a portion of a fluid-filled tube, such as an umbilical cord, when the cord is positioned within the sleeve. Specifically, an umbilical cord may be positioned within the elastic sleeve. The sealing sleeve may include a cord-engaging portion and a base portion. The cord-engaging portion permits the insertion of the umbilical cord or other fluid-filled tube and functions as a cord-sealing portion to seal to an exterior surface of the inserted umbilical cord. The base portion functions as a drain-sealing portion to seal relative to the drain so that the sealing sleeve functions to seal the open end of an umbilical cord relative to the drain. The sleeve may be twisted or moved starting from the cord-engaging portion towards the base portion to lightly engage the umbilical cord or fluid-filled tube. As the sealing sleeve is twisted about the cord, the sealing sleeve sealably engages the exterior of the cord and thereby seals the open end of the umbilical cord relative to the drain. A base or support may be provided to support the sleeve in a desired position, for example, to receive the open end of an umbilical cord to permit drainage of fluid from such open end. The actuator communicates with the sleeve so that movement of the actuator causes movement of the sleeve so as to decrease the diameter of the sleeve until the sleeve sealably engages an outer circumferential surface of the umbilical cord. The actuator may include a handle that enables easier movement of the actuator. The actuator may be positioned or supported relative to the base so that movement of the actuator enables the sleeve or elastic tubing to surround and engage the umbilical cord to seal the seal member with the umbilical cord to facilitate drainage of fluids from the umbilical cord towards a drain. Specifically, as material flows from the cord through the drain, sealable engagement of the seal member with the cord and relative to the drain prevents overflow of material out of the apparatus.

In accordance with the present invention, a method is provided for collecting fluid from a tube such as a vein, vessel, cord member or other tubular member filled with fluid. The method may include surrounding an umbilical cord with a seal member such as an elastic or deformable sleeve; sealably engaging the sleeve with the cord by, for example, adjusting the sleeve into sealed engagement with the cord; sealing the sleeve relative to the drain; draining material from the cord and into the drain; and collecting material drained from the cord.

BRIEF DESCRIPTION OF THE DRAWINGS

The foregoing summary as well as the following description of the present invention will be better understood when read in conjunction with the figures in which:

FIG. 3 is a schematic side elevation diagram of one configuration of an umbilical cord harvester in accordance with the present invention wherein an umbilical cord is positioned within a seal member directly communicating with a drainage tube.

DETAILED DESCRIPTION

Referring now to the Figures in general, wherein like reference numbers refer to the same components across the several views, there is shown an apparatus, generally designated 10, for harvesting biological material from an umbilical cord. In general application, the apparatus 10 may be used to drain biological material from a fluid-filled tube such as a vein, vessel, cord member or other tubular member. In specific application, the apparatus 10 may be used to drain biological material, including fluid, blood, cells, and specifically stem cells, from an umbilical cord. Preferably, the apparatus 10 may be used to drain biological material from across the entire diameter of the umbilical cord.

Figure 1:
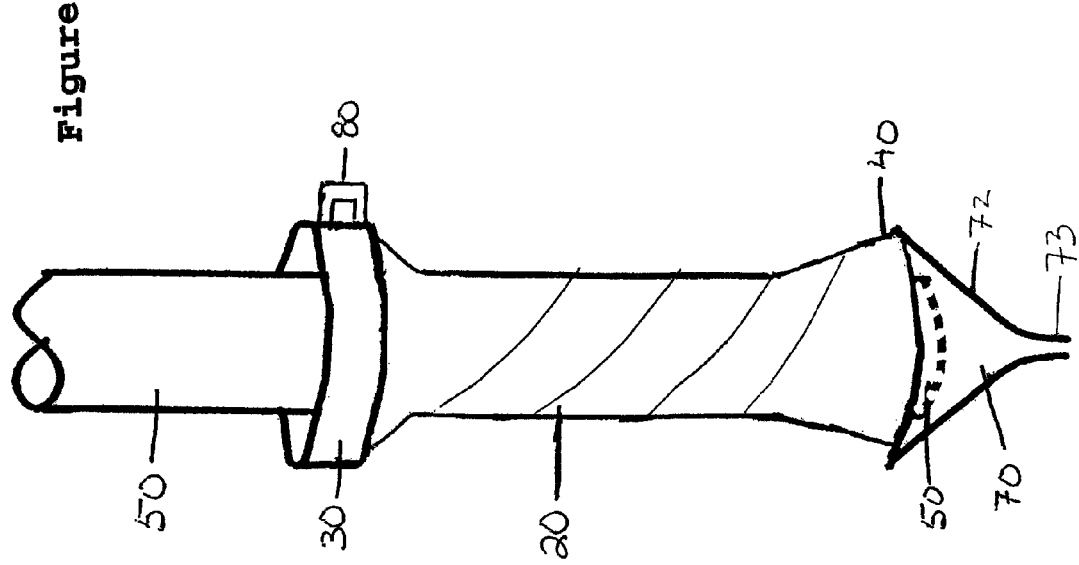
FIG. 1 is a schematic side elevation diagram of one configuration of an umbilical cord harvester in accordance with the present invention wherein an umbilical cord is positioned within a seal member.

As shown in FIG. 1, the apparatus 10 includes a drain 70, such as a funnel 72 and tube 73 as shown in FIG. 1 or, as shown in FIG. 3, a drain tube 90 without a funnel for draining material from an open end of an umbilical cord 50. When a child is delivered, the umbilical cord is clamped and cut. The cut, or open, end of the umbilical cord is inserted into the apparatus so material and fluid drain from the open end of the cord through the drain. The drain 70 may include a funnel-shaped drain structure for fluid collection to provide a temporary reservoir during drainage. Alternatively, the drain may include a drainage tube 90 without a funnel as shown in FIG. 3. As material and/or fluid drains from the umbilical cord, the material and fluid flow through the funnel or tube. A user may position a bag or collection bin relative to the funnel 70 or tube 90 to collect biological material. By monitoring the amount of material flowing into the collection bin, medical personnel can remove the collection bin once an appropriate amount of material has been collected, thereby decreasing the likelihood of over-filling a collection bag or trapping air within the collection bag. Use of a drain or tube in a sealed relationship with the open end of the umbilical cord is much easier for medical personnel to collect material from a cord as compared to traditional methods. Another advantage of using a sealed drain 70 or tube 90 to channel fluid and material from the umbilical cord is that the increased flow rate of materials from the umbilical cord decreases the likelihood that biological materials will coagulate within the collection bag. Also, by using an actuator to adjustably engage the seal member with an outer circumference of an umbilical cord, the apparatus may be used with umbilical cords of varying diameters.

A seal member 20 may be provided in sealed or sealable communication with the drain 70. The seal member 20 may be sealed to or bonded with the drain 70 to prevent overflow or spillage of biological material out of the apparatus at the funnel or drain. A drain may be utilized having a larger diameter spout than an inlet for a collection bag. Since a wide-mouthed drain such as a funnel may be able to accommodate more fluid as compared to the relatively narrow inlet of a collection container, materials may flow out of the umbilical cord and be held in the reservoir of the funnel until such material can drain into the collection bin. When material flows from the umbilical cord at a faster rate, the outlet at the base or bottom of the funnel may become clogged or congested with material. The clogged drain may tend to cause material to overflow the mouth of the funnel or drain. Accordingly, by sealing the seal member 20 directly to the drain 70, such as the mouth of the funnel in FIG. 1 or directly to the drain tube in FIG. 3, the overflow from the drain will be contained within the sealed environment created by the seal member. For example, by sealably bonding the seal member 20 with the drain 70, material from the cord will not overflow or leak since the seal member also sealably engages the exterior surface of the cord. Likewise, material cannot leak out from the seal member 20 or the drain 70. Additionally, in selected applications, the seal member 20 may also be moved, pinched, twisted, or otherwise distorted to securely engage the cord, thereby restricting or retarding the flow of material and fluid from the cord and thereby preventing overflow of biological material.

Figure 2:
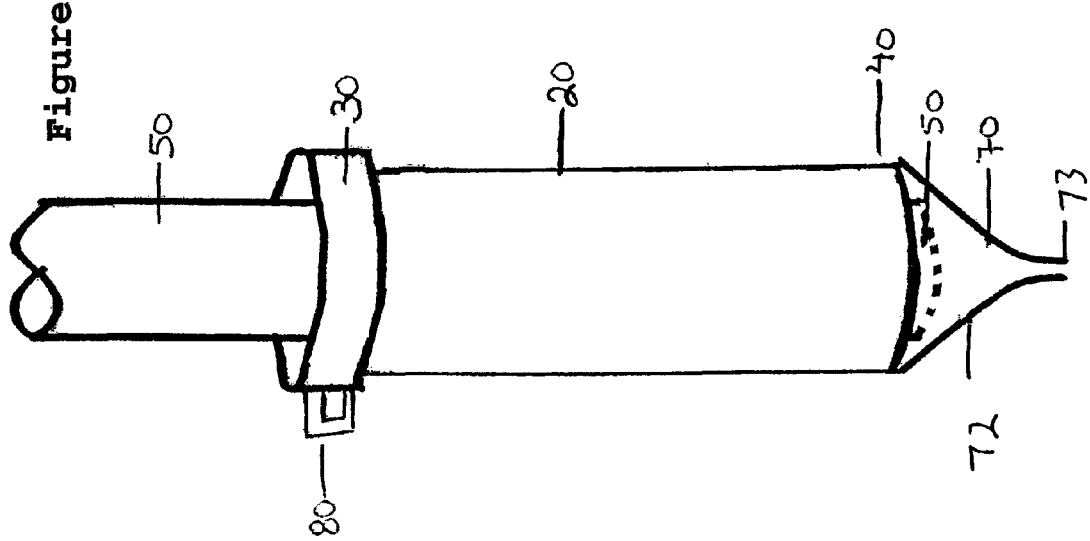
FIG. 2 is a schematic side elevation diagram of one configuration of an umbilical cord harvester as shown in FIG. 1 wherein the seal member twists about an umbilical cord to seal to an exterior surface of the cord.
Figure 5:
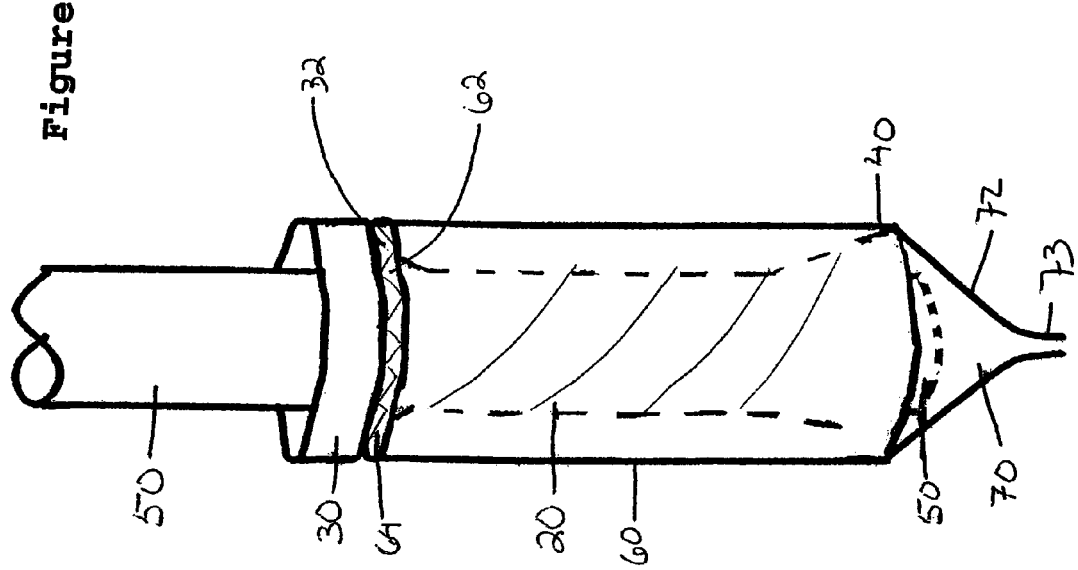
FIG. 5 is a schematic side elevation diagram of one configuration of an umbilical cord harvester shown in FIG. 4 wherein an umbilical cord is positioned within the seal member and the support tube, such that the seal member twists about the umbilical cord to seal to an exterior surface of the cord.
Figure 4:
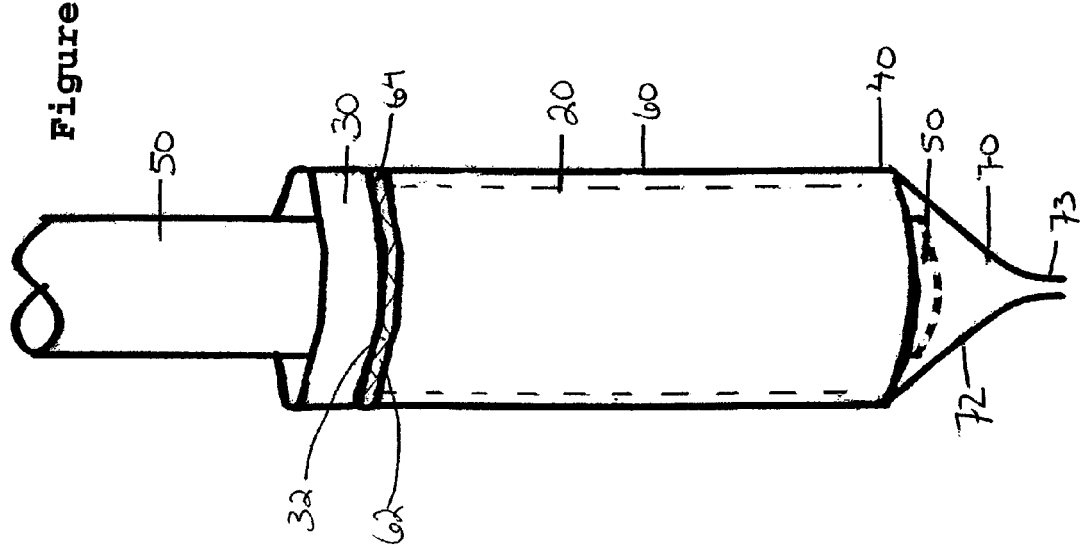
FIG. 4 is a schematic side elevation diagram of one configuration of an umbilical cord harvester in accordance with the present invention wherein an umbilical cord is positioned within a seal member and a support tube.

Sealing of the seal member relative to the umbilical cord and the drain facilitates the drainage and collection of biological materials from the umbilical cord. The seal member may include a drain-sealing portion 40 for sealing with the drain or relative to the drain. FIGS. 1-2 show a drain 70 in sealed communication with the sealing portion of the seal member 20. FIG. 3 shows a drain tube 90 in direct sealed communication with the seal member 20 whereby the drain-sealing portion 40 of the seal member sealably engages the drain tube 90. FIGS. 4-5 show the drain-sealing portion 40 of the sealing member in sealed communication with the open mouth of a drain funnel 70. In a preferred configuration, the seal member 20 is directly bonded, attached to, or sealed to the drain 70.

The seal member seals the open end of the umbilical cord in relation to the drain. The seal member 20 may include, for example, an elastic, sealing sleeve capable of sealed communication with a fluid-filled tube-like structure such an as umbilical cord 50. The adjustable sleeve may be dimensioned to generally conform about the external surface of a section of an umbilical cord. While any selected portion of the umbilical cord may be used in conjunction with the apparatus 10, the open end of the umbilical cord may be placed within the seal member. For example, the umbilical cord may be positioned within the seal member 20 with the open end of the cord intermediate the ends of the sealing sleeve or the cord may extend the entire length of the seal member 20 with the open end of the cord disposed at, near, or even beyond the end of the sleeve. As depicted in FIG. 1, the umbilical cord 50 extends beyond the length of the seal member 20 into the drain 70 thereby maximizing the area of sealing contact between the seal member and the exterior surface of the umbilical cord. FIG. 1 depicts the cut-end of the umbilical cord contained within the apparatus 10 and is shown in phantom by a dotted line. Adjusting the position of the seal member 20 relative to the umbilical cord may cause the seal member to surround, twist about, and/or lightly engage the cord 50 as desired to seal to the cord.

In order to facilitate movement, e.g., twisting and turning, of the seal member 20 about the umbilical cord 50, the seal member may be constructed of a flexible material capable of twisting and/or folding about itself. For example, the seal member 20 may be constructed from plastic, rubber, elastic or other flexible material. Since the seal member 20 is flexible and stretchable, the member is able to accommodate umbilical cords of varying sizes. In one embodiment, the seal member may have an opening having a diameter of approximately 1-1.5 inches; however, the member may be able to accommodate cords of varying sizes such as by twisting about the cord. As depicted in FIG. 2, twisting the seal member 20 decreases the diameter of the seal member and thereby causes the seal member to twist around and sealably engage the cord 50.

Although the seal member 20 may be twisted to sealably engage the exterior surface of the umbilical cord, the seal member 20 may also be pinched, squeezed, compressed, or otherwise moved to sealably engage the umbilical cord. For instance, the seal member 20 may include a sealable sleeve such as elastic tubing for moving or twisting around an umbilical cord. Alternatively, the sleeve may be constructed from rubber, plastic or other flexible material capable of twisting about itself or desirably capable of deformation or elastic deformation in order to engage and seal against the umbilical cord. An elastic property of the sleeve 20 may optionally facilitate the ability of the sleeve to twist about the umbilical cord. The sleeve 20 may surround and enclose the cord and then be twisted or moved into sealing engagement with the cord. In one embodiment, the sleeve 20 may include a cord-sealing portion for receiving the umbilical cord or other fluid-filled tube. The elastic sleeve 20 may also include a drain-sealing portion for sealing with or relative to the drain. The cord-sealing portion may be movable relative to the drain-sealing portion to enable the sleeve to be distorted or twisted from the cord-sealing portion towards the drain-sealing portion. For example, if the drain-sealing portion is sealed and held in position relative to the drain and the cord-sealing portion is twisted relative to the drain-sealing portion, the inside diameter of the sleeve 20 will contract in a direction commencing from, at or near the cord-sealing portion of the sleeve towards the drain-sealing portion until the cord-sealing portion of the sleeve engages and seals to the exterior surface of the umbilical cord. In general, however, the cord-sealing portion is moved or adjusted into sealing communication with the exterior circumference of the cord.

A support 40 may be provided to support the seal member 20 in a selected orientation or position. As provided in FIG. 1, the support 40 may include a base support ring or section, such as an annular support base, at the drain end of the seal member 20. In this regard, FIG. 1 depicts the support 40 as a circular ring at the top or open mouth of the funnel 70. The support 40 may also be square or any other shape so that an opening is provided through which material and fluid may drain from the umbilical cord 50 into the drain. The support 40 may also be positioned along the seal member 20 at any suitable position. The support 40 may be constructed as a separate component fixed onto or connected with the seal member 20. In another embodiment, the support 40 may include separate support members, such as support legs or other structure such as a tubular support to support the seal member 20 in a desired position.

An actuator may be provided to actuate or facilitate actuation or adjustment of the seal member so that the seal member moves into engagement with the umbilical cord to seal the seal member relative to the umbilical cord 50. The actuator 30 may be attached or positioned relative to the seal member 20 so that movement of the actuator moves the seal member 20 and preferably moves the seal member into sealed engagement with an exterior surface of the umbilical cord. The actuator 30 may be positioned along the length of the seal member 30 or at an end of the seal member. Although FIG. 1 shows the actuator 30 positioned at an end of the seal member 20, the actuator 30 may be positioned at any selected point along the seal member 20. As depicted in FIG. 1, the actuator may include an actuator ring in communication with the seal member 20. In FIG. 1, an upper end of the cord-sealing portion of the seal member is connected with or attached to the actuator ring. While the actuator 30 is depicted as a circular ring, the actuator may be square or any other shape having an opening able to accommodate the umbilical cord. Optionally, the actuator 30 may also include a handle for ease of maneuvering the actuator. For example, a handle 80 may be provided on the actuator to assist a user to easily move and/or twist the seal member to sealably engage the umbilical cord 50. The handle communicates with the sealing sleeve and may be positioned relative to the base to effect sealing of the seal member to the umbilical cord. Preferably, the handle 80 can be moved by the user to turn the actuator 30 relative to base 40 to twist a top portion or a cord-sealing portion of the sleeve 20 into sealed engagement with the circumferential exterior surface of the umbilical cord while the base 40 holds the bottom portion or drain-sealing portion of the sleeve in position to permit the sleeve to be twisted by the actuator into sealed engagement with the circumferential outer surface of the umbilical cord.

Movement of the actuator 30 relative to the support 40 moves the seal member 20 and thereby facilitates engagement of the seal member 20 with the umbilical cord 50. As shown in FIGS. 1 and 2, the actuator 30 may be moved relative to the position of the support 40, thereby distorting or twisting the seal member 20. Specifically, rotational movement of the actuator 30 relative to the support 40 causes the seal member 20 to twist and/or wrap around and thereby seal to the umbilical cord 50. FIG. 2 shows that twisting the actuator 30 relative to the support 40 wraps the seal member 20 about the cord 50. Engaging the seal member 20 with the cord 50 prevents any overflow of material in the event that the drain or tube from the apparatus becomes clogged or if biological material drains out of the umbilical cord a greater rate than the flow of material through the drain or tube. The tighter the actuator 30 twists the seal member around the cord 50 the tighter the seal becomes. Specifically, a great deal of distortion of the seal member 20 may even decrease or even completely stop the flow of biological material from the umbilical cord. For instance, if the seal member 20 is wrapped very tightly around the cord 50, little, if any, biological material may be collected as compared to the seal member 20 loosely engaging or even simply surrounding the cord. The seal member 20 may be positioned to engage the cord with a selected degree of tightness. In general, however, the seal member 20 functions to seal against the umbilical cord 50.

Turning to FIGS. 4 and 5, an alternate embodiment of an apparatus is provided. A support tube 60 may be positioned external to the seal member 20 for supporting the seal member, for example, in a generally upright manner. The support tube may be constructed from plastic or other material and preferentially may be constructed from a clear material so that a user can view the umbilical cord contained within the seal member 20 and the material draining from the cord. Preferentially, the support tube 60 is constructed of a durable or a rigid or semi-rigid material to surround and protect the seal member from becoming ripped, torn or otherwise damaged. Similarly, the support tube 60 protects a user from contacting biological material in the event the seal member develops tears, leaks, or ruptures.

The support tube 60 engages the actuator 30 along interface 64. Actuation of the actuator 30 relative to the support tube 60 effects the adjustable engagement of the seal member 20 with the umbilical cord. The seal member 20 is positioned within the support tube 60 and is depicted in FIGS. 3 and 4 in a phantom view by a series of dotted lines. The top or cord-sealing portion of the sleeve-like seal member is connected with the actuator. The bottom or drain-sealing portion of the sleeve like seal member is sealed and fixed to the base of the support tube, such as along the inside diameter of the support tube, or alternatively to the top of the funnel, or as a further alternative is sandwiched and sealed between the top of the funnel and the bottom of the support tube. Actuation of the actuator causes the seal member to sealably engage with the cord. FIG. 4 shows engagement of the seal member 20 with the umbilical cord 50 while positioned within the protective support tube 60. As the actuator is twisted, the seal member 20 twists and moves around the umbilical cord 50 so that a seal is formed between the seal member and the cord to prevent overflow of material out of the apparatus and at the drain funnel.

Optionally, a set of cogs may be provided at the interface 64 to enable the actuator 30 and the support tube 60 to movably interact relative to one another along the interface 64. In this regard, actuator cogs 32 may be positioned along or at a lower portion of the actuator 30. The cogs 32 may be positioned in a ring or track around or along the actuator 30, for example, along the bottom rim of the ring-like actuator. The actuator cogs 32 function to mate with or track support cogs 62 positioned along an upper portion of the support tube 60. The support cogs may be positioned in a ring or track along the support tube 60 to mate with the actuator cogs to enable controlled movement of the actuator relative to the support tube. The support cogs may be positioned along the upper rim of the support tube 60. The cogs 32, 62 may be configured to allow for a ratchet-like motion of the actuator 30 relative to the support tube 60, thereby providing a controlled positioning of the actuator relative to the support tube.

The ratchet motion of the actuator 30 relative to the support tube 60 provides the user with control over maintaining the position of the seal member 20 relative to the umbilical cord. Moving the actuator 30 causes the seal member 20 to tighten and seal against the umbilical cord 50. The actuator cogs 32 mated with support cogs 62 may securely maintain the position of the actuator 30 relative to the position of the support tube 60. Mating the actuator cogs 32 with the support cogs 62 may be particularly useful when a user wishes to maintain a degree of tightness of the seal member 20 upon the umbilical cord 50. No additional adjustments may be needed to maintain a desired position of the seal member 20 after the actuator is twisted into a desired position along the top of the support tube. Specifically, once properly adjusted, the seal member 20 may remain at a selected degree of tightness around the umbilical cord 50, for example, to maintain a seal with the umbilical cord, without any further adjustments from the user.

Figure 6:
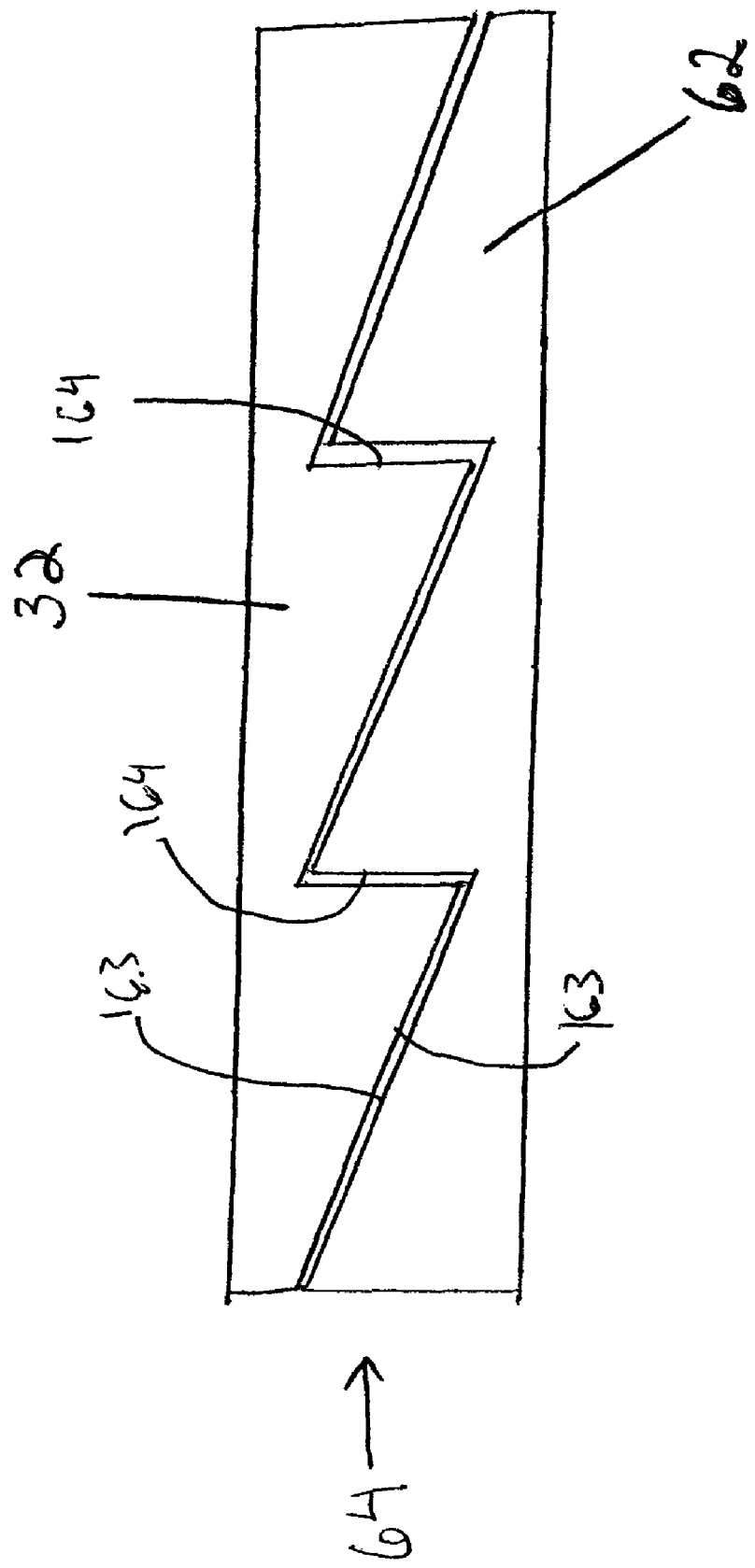
FIG. 6 is an enlarged side elevation diagram, in partial section, of one configuration of an interface between an actuator and the support tube of the umbilical cord harvester shown in FIGS. 4 and 5.

The shape of the cogs 32, 62 enhances the controlled, relative movement of the actuator relative to the support tube. The actuator cogs 32 and support cogs 62 may have a wedge shape as shown in FIG. 6. For instance the cogs 32, 62 may have an angled cam portion 163 and a vertical stop portion 164. The angled portion of the actuator cog 32 may engage the angled portion of the support cog 62 to allow slidable movement of the sets of cogs along such angled ramp portions 163. The interspersed stop portions function to prevent reverse movement of the cogs 32, 62, thereby halting reverse or backwards movement of the actuator 30. For example, rotational movement of the actuator 30 relative to the support tube 60 enables the actuator cog 32 to move along an angled ramp portion of the support cogs from the right side of the diagram shown in FIG. 6 towards the left side. Rotational movement of the actuator in the opposite direction is prohibited by the stop portions which move into abutment with one another and stop further relative movement in the opposite direction. For example, in terms of FIG. 6, the stop portion 164 of the cogs prevents movement of the actuator cog 32 in a direction from the left side to the right side of FIG. 6. Accordingly, the actuator cogs and support cogs provide for rotational movement of the actuator is one rotational direction, which in turn provides for controlled twisting and distortion of the seal member but prevent rotational movement in the opposite direction.

Specifically, the actuator 30 may also be moved in an axial direction away from the support tube 60. In this regard, the elasticity of the seal member connected between the actuator ring and the base of the support tube may permit the actuator to be moved or pulled away from the support tube against the elasticity of the seal member so as to permit the actuator cogs to move in a direction up the ramp of the support cogs that tends to disengage the actuator cogs from the support cogs. Complete disengagement of the cogs may also be permitted. In terms of FIG. 6, as the actuator cogs move along the support cogs, the actuator moves not only towards the left of the diagram but also in an upward, axial direction to allow the angled ramp portions 163 to clear one another. Once the actuator cog 32 reaches the top of the angled portion, the elasticity of the seal member may function to snap the actuator back into tighter engagement with support tube and into a cog 32 interlocking position as shown in FIG. 6 where the stop portions 164 of the cogs prevent backward or reverse movement. Snapping the actuator cogs into an interlocking position relative to the support cogs may be enhanced by the elastic nature of the seal member 20. Accordingly, once a user positions the actuator at a desired position relative to the support tube, the seal member 20 snaps the cogs together at an interlocking portion of the track. Accordingly, as the actuator is rotated relative to the support tube the mating cogs function to permit rotational movement in one direction but prevent rotational movement in the other direction. In use, the cogs function to permit the actuator to move in a direction to more tightly twist the seal member about the umbilical cord to effect the desired degree of sealing but prevent reverse relative motion to thereby stop any backlash motion of the actuator that might otherwise be caused by the twisting seal member that would otherwise tend to reduce the amount of squeeze or sealing on the umbilical cord. As such, a sealed engagement of the seal member to the umbilical cord can be created and maintained.

A method for collecting fluid from a fluid-filled tubular member is also provided. Specifically, a method is provided for collecting biological material from an umbilical cord. First, a portion of the umbilical cord is surrounded by a seal member. The seal member may have a tube-like shape such as an elastic or movable sleeve that may be positioned over the umbilical cord. Once the seal member surrounds the umbilical cord, the seal member may be twisted, moved, and/or otherwise distorted or adjusted into sealed communication with the umbilical cord. Specifically, the seal member sealably engages the umbilical cord and is sealed relative to a drain so that material flows from the cord into the drain without any overflow or leakage of material. In selected uses, the seal member may be positioned or moved relative to the umbilical cord to slow or halt the flow of biological material from the umbilical cord. The biological material is drained from the umbilical cord and into the drain. The biological material may be collected in a storage bag or other container.

In one embodiment, the step of draining the biological material from the cord may be synchronized with the step of collecting the biological material. It may be also desired to enhance engagement of the seal member with the umbilical cord at desired lengths or in a desired manner to provide an effective seal between the open end of the umbilical cord and the drain. Furthermore, an in utero umbilical cord may be used in connection with the claimed invention. Specifically, once a child has been delivered but before the placenta has been delivered, the umbilical cord may be cut, thereby separating the child from the mother, and the newly-cut end of the umbilical cord may be inserted into the apparatus. The placenta may deliver materials to and through the umbilical cord for collection. Accordingly, the seal member may effectively seal the open end of the umbilical cord relative to the drain to create a sealed environment to prevent leakage or overflow of materials. In another embodiment, a user may alternatively tighten and loosen the seal member against the umbilical cord to increase or enhance the amount of material collected. A user might agitate the biological material already collected to promote an even consistency of materials and fluids. Also, agitating the biological material may also prevent coagulation of the biological material already collected.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An apparatus for collecting biological material from an umbilical cord, comprising:
   a drain for draining material from an open end of an umbilical cord;
   a seal member for sealing the open end of the umbilical cord in relation to the drain,
   wherein the seal member sealably engages at least a portion of an exterior surface of the cord and wherein the seal member is configured to twist from one end of the seal member relative to the other end of the seal member along the length of such portion of the cord to form a seal relative to the cord; and
   an actuator for adjusting the seal member to effect sealed engagement of the seal member with the umbilical cord so that biological material flows from the open end of the umbilical cord through the drain.

2. The apparatus of claim 1, wherein the drain includes a funnel in sealed communication with the seal member, wherein the funnel receives biological material from the umbilical cord in a sealed manner.

3. The apparatus of claim 1, including a support for supporting the seal member at a desired position relative to the open end of the umbilical cord.

4. The apparatus of claim 3, including:
   actuator cogs positioned along a portion of the actuator; and
   support cogs positioned along a portion of the support;
   wherein the actuator cogs mate with the support cogs to enable the actuator to move in a selected direction relative to the support.

5. The apparatus of claim 4, wherein the actuator cogs mate with the support cogs to enable the actuator to move the seal member relative to the support and the umbilical cord to effect a seal with the umbilical cord.

6. The apparatus of claim 5 including a drain funnel, wherein the seal member includes a sleeve having one end fixed relative to the drain funnel to seal the sleeve to the drain funnel and another end fixed relative to the actuator so that turning of the actuator twists the sleeve about the umbilical cord from the actuator end of the sleeve towards the drain funnel end of the sleeve into sealed engagement with the umbilical cord.

7. The apparatus of claim 4, wherein the seal member includes an elastic material and the elasticity of the seal member enhances engagement of the actuator cogs and the support cogs into a selected interlocking position.

8. The apparatus of claim 1, wherein the seal member includes elastic material.

9. The apparatus of claim 8, wherein the actuator is configured to move the seal member to decrease the diameter of a sleeve to move into sealed engagement with the umbilical cord.

10. An apparatus for collecting fluid from an umbilical cord, comprising:
  a drain for collecting fluid extracted from an umbilical cord;
  a sealing sleeve for sealing an open end of the umbilical cord with the drain, the sealing sleeve including an adjustable cord-sealing portion for adjustably sealing to an exterior surface of the umbilical cord and a drain-sealing portion for sealing relative to the drain, wherein the sleeve sealably engages at least a portion of the exterior surface of the cord and wherein the sleeve is configured for being twisted from one end of the sleeve relative to the other end of the sleeve along the length of such portion of the cord into sealed contact with the umbilical cord;
  a support communicating with the sealing sleeve; and
  an actuator communicating with the sealing sleeve capable of being positioned relative to the support to induce the cord-sealing portion of the sealing sleeve to engage and seal against an exterior surface of the umbilical cord to effect sealed drainage of fluid from the open end of the umbilical cord into the drain.

11. The apparatus of claim 10, wherein the actuator effects movement of the cord-sealing portion of the sealing sleeve into sealed engagement with the umbilical cord.

12. The apparatus of claim 10, wherein the drain-sealing portion of the sleeve is fixed relative to the drain to seal the sleeve to the drain and wherein the cord - sealing portion of the sleeve is fixed relative to the actuator so that turning of the actuator twists the sleeve about the umbilical cord from the actuator end of the sleeve towards the drain end of the sleeve into sealed engagement with the umbilical cord.

13. The apparatus of claim 12, wherein the actuator effects twisting of the sleeve and thereby decreases the diameter of the sleeve into sealed engagement with the umbilical cord.

14. The apparatus of claim 10, wherein the drain is in sealed communication with the drain-sealing portion of the sleeve.

15. The apparatus of claim 10, wherein the drain includes a funnel having a mouth, wherein the mouth of the funnel is sealed relative to the drain-sealing portion of the sealing sleeve.

16. The apparatus of claim 10, wherein the support includes a support tube for supporting the sealing sleeve within the support tube in position to receive and hold the open end of the umbilical cord so that biological material from the umbilical cord flows toward the drain.

17. A method for collecting biological material from an open end of an umbilical cord, comprising:
  adjustably engaging a seal member with the umbilical cord;
  sealing the seal member relative to a drain to seal the open end of the umbilical cord relative to the drain, wherein the sealing step includes sealably engaging the seal member with at least a portion of the exterior surface of the cord by twisting the seal member from one end of the seal member relative to the other end of the seal member along the length of such portion of the cord to form a seal relative to the cord;
  draining biological material from the umbilical cord into the drain; and
  collecting the biological material drained from the umbilical cord.

18. The method of claim 17, wherein the step of draining biological material from the umbilical cord is synchronized with the step of collecting the biological material.

* * * * *